United States Patent
Schaus et al.

(10) Patent No.: US 6,355,674 B1
(45) Date of Patent: Mar. 12, 2002

(54) AMINOTETRALINS AS 5-HT$_{1D\alpha}$ AGONISTS

(75) Inventors: John M Schaus, Zionsville; Clint D Walker, Indianapolis; Yao-Chang Xu, Fishers, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/403,854

(22) PCT Filed: Apr. 27, 1997

(86) PCT No.: PCT/US98/08436

§ 371 Date: May 2, 2000

§ 102(e) Date: May 2, 2000

(87) PCT Pub. No.: WO98/48786

PCT Pub. Date: Nov. 5, 1998

Related U.S. Application Data

(60) Provisional application No. 60/093,060, filed on Apr. 30, 1997, now abandoned.

(51) Int. Cl.[7] .............. C07C 211/42; C07D 309/04; C07D 309/20; C07D 307/14; C07D 307/28

(52) U.S. Cl. .............. 514/450; 549/426; 549/491; 549/346; 514/459; 514/471; 514/675

(58) Field of Search ................. 549/426, 491, 549/346; 564/428; 514/450, 459, 471, 657

(56) References Cited

U.S. PATENT DOCUMENTS

| | | | |
|---|---|---|---|
| 5,047,422 A | 9/1991 | Junge et al. | 514/510 |
| 5,286,753 A | 2/1994 | Schaus et al. | 514/657 |
| 5,545,755 A | 8/1996 | Lin et al. | 564/428 |
| 5,571,942 A | 11/1996 | Hoechstetter et al. | 564/428 |

OTHER PUBLICATIONS

*J. Med. Chem.*, Kline, et al., vol. 33, pp. 950–955 (1990).
*J. Med. Chem.*, Liu, et al., vol. 36, pp. 4221–4229 (1993).
Sternfeld et al. Journal of Medicinal Chemistry, 1999, vol. 42, 677–690.*

* cited by examiner

*Primary Examiner*—Mark L. Berch
*Assistant Examiner*—Kahsay Habte
(74) *Attorney, Agent, or Firm*—Charles T. Joyner; Nelson L. Lentz

(57) ABSTRACT

A class of novel aminotetralins is disclosed useful as 5-HT$_{1D\alpha}$ agonists.

7 Claims, No Drawings

AMINOTETRALINS AS 5-HT$_{1D\alpha}$ AGONISTS

This is a 371 of PCT/US98/08436 filed Apr. 27, 1998 which claims priority to U.S. Provisional Application No. 60/093,060, filed Apr. 30, 1997.

BACKGROUND OF THE INVENTION

This invention relates to novel substituted aminotetralins useful as 5-HT$_{1D}$ agonists.

Over the last several years it has become apparent that serotonin (5-hydroxytryptamine; 5-HT) is associated directly or indirectly with a number of physiological phenomena, including appetite, memory, thermo-regulation, sleep, sexual behavior, anxiety, depression, and hallucinogenic behavior [Glennon, R. A., J. Med. Chem. 30, 1 (1987)].

5-HT receptors have been identified in the central nervous system (CNS; brain and spinal cord) and in peripheral tissues including the gastrointestinal tract, lung, heart, blood vessels, and various other smooth muscle tissues.

It has been recognized that there are multiples types of 5-HT receptors. These receptors have been classified as 5-HT$_1$, 5-HT$_2$ and 5-HT$_3$ receptors, with the former being further divided into the sub-classes 5-HT$_{1A}$, 5-HT$_{1B}$, 5-HT$_{1C}$, 5-HT$_{1D}$, 5-HT$_{1E}$, and 5-HT$_{1F}$.

Within the 5-HT$_1$ receptor class, several subtypes have been distinguished on the basis of their pharmacological binding profiles, second messenger coupling and physiological roles. One such subtype, the 5-HT$_{1D}$ receptor, was originally defined as a particular type of [$^3$H]5-HT binding site in the bovine caudate (Heuring and Peroutka, J. Neurosci., 7:894 (1987)).

Few ligands have selectivity for 5-HT$_{1D}$ receptors. Sumatriptan possesses limited 5-HT$_{1D}$ selectivity. GR 127935 has also been identified as a patent and selective 5-HT$_{1D}$ receptor antagonist. Hayer, et al., *Pharmacological Reviews*, Vol. 46, No. 2, pp. 157–203 (1994).

Molecular cloning has demonstrated that pharmacologically defined $^5$-HT$^{1D}$ receptors are encloded by two separate but closely related genes, designated 5-HT$_{1D\alpha}$ and 5-HT$_{1D\beta}$, which are members of the GPRC superfamily. These receptors display highly conserved transmembrane homology (75%) and similar binding properties and second messenger coupling (inhibition of adenylate cyclase). Leonhardt, S., et al., *J. Neurochem,* 53:465–471 (1989).

The 5-HT$_{1D\alpha}$ receptor is a species homolog of the 5-HT$_{1D}$ receptor of bovine calif caudate and guinea-pig brain. Hartig, et al., supra.

The 5-HT$_{1B}$ and 5-HT$_{1D\beta}$ receptors have recently been shown to be species homologues of the same receptor subtype. They display similarities in their pharmacology, second messenger coupling, and anatomical distribution. The 5-HT$_{1B}$ subtype appears to be confined to rat, mouse, and opossum whereas 5-HT$_{1D\beta}$ sites have been demonstrated in human, pig, guinea pig and calf. Adham, N., et al., *Mol. Pharmacol.,* 41:1–7 (1992).

The rat 5-HT$_{1B}$ receptor differs from its human counterpart at only 4% of its transmembrane amino acids, but its pharmacological binding properties are dramatically different from those of the human $^5$-HT$_{1DB}$ receptor. Hartig, et al., *Trends Pharmacol. Sci.,* 13:152–159 (1992).

We have now discovered a further class of compounds which have selective 5-HT$_{1D\alpha}$ agonist activity useful in treatment of dementia, Parkinson's Disease, appetite modulation, anxiety, migraine, sexual dysfunction, irritative bladder symptoms of benign prostatic hyperplasia, urge incontinence and excessive bladder activity caused by bacterial cystitis, interstitial cystitis, radiation/chemotherapy-induced cystitis, outlet obstruction, neurogenic bladder, spinal cord injury, stroke, and nocturnal enurisis.

It is desirable to develop new compounds and treatments for these 5-HT$_{1D\alpha}$ mediated diseases.

This invention provides a compound of formula I

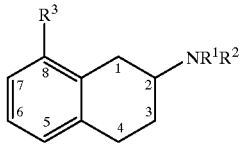

(I)

wherein:

R$^1$ and R$^2$ are each individually hydrogen or —(C$_1$–C$_6$)alkyl;

R$^3$ is —(C$_2$–C$_8$)alkenyl, —(CH$_2$)$_q$(C$_3$–C$_8$)cycloalkyl —(CH$_2$)$_n$O(CH$_2$)$_p$R$^5$,

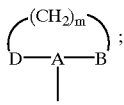

;

or

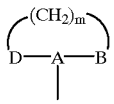

substituted with one substituent selected from the group consisting of —(C$_1$–C$_6$)alkyl and —(C$_3$–C$_8$)cycloalkyl;

where

A—B is >C=CH— or >CR$^4$CH$_2$—;

D is —CH$_2$— or oxygen;

R$^4$ is hydrogen or —OH;

R$^{5'}$ is —(C$_3$–C$_8$)cycloalkyl, or phenyl substituted with one substituent selected from the group consisting of halo, —(C$_1$–C$_6$)alkyl and (C$_1$–C$_6$)alkoxy;

m is an integer from 1 to 5 both inclusive;

n is an integer from 0 to 4 both inclusive;

p is an integer from 1 to 7 both inclusive; and q is an integer from 0 to 4 both inclusive;

or a pharmaceutically acceptable salt or optical isomer thereof;

provided that when D is oxygen, >A—B is not >C=CH—; and when R$^4$ is —OH, D is oxygen.

This invention also provides a pharmaceutical formulation comprising a compound of formula I in association with one or more pharmaceutically acceptable diluents, carriers and excipients.

This invention further provides a method of activating the 5-HT$_{1D\alpha}$ receptor comprising administering to a mammal in need of such treatment a therapeutically effective amount of a compound of formula II

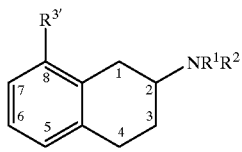

(II)

wherein:
$R^1$ and $R^2$ are each individually hydrogen or —$(C_1-C_6)$alkyl;
$R^{3'}$ is —$(C_1-C_8)$alkyl, —$(CH_2)_q(C_3-C_8)$cycloalkyl, —$(C_2-C_8)$alkenyl, —$(C_1-C_8)$alkan-1-ol-1-yl, —$(CH_2)_nO(CH_2)_pR^{5'}$,

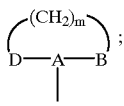

or

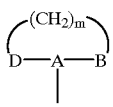

substituted with one substituent selected from the group consisting of —$(C_1-C_6)$alkyl and —$(C_3-C_8)$cycloalkyl;
where
A—B is >C=CH— or >$CR^4CH_2$—;
D is —$CH_2$— or oxygen;
$R^4$ is hydrogen or —OH;
$R^{5'}$ is —$(C_1-C_6)$alkyl, —$(C_3-C_8)$cycloalkyl, —$(C_1-C_6)$alkoxy, phenyl or phenyl substituted with one substituent. selected from the group consisting of halo, —$(C_1-C_6)$alkyl and $(C_1-C_6)$alkoxy;
m is an integer from 1 to 5 both inclusive;
n is an integer from 0 to 4 both inclusive;
p is an integer from 1 to 7 both inclusive; and
q is an integer from 0 to 4 both inclusive;
or a pharmaceutically acceptable salt or optical isomer thereof;
provided that when D is oxygen, >A—B is not >C=CH—.

This invention also provides a method of alleviating the pathological effects of 5-HT$_{1D\alpha}$ receptor-activated diseases which comprises administering to a mammal in need of such treatment a therapeutically effective amount of the compound of formula II.

A still further aspect of the invention is a method of treating a mammal suffering from or susceptible to any condition activated by the 5HT$_{1D\alpha}$ receptor of the type represented by dementia, Parkinson's disease, anxiety, migraine, appetite modulation, sexual dysfunction, irritative bladder symptoms of benign prostatic hyperplasia, urge incontinence and excessive bladder activity caused by bacterial cystitis, interstitial cystitis, radiation/chemotherapy-induced cystitis, outlet obstruction, neurogenic bladder, spinal cord injury, stroke and nocturnal enurisis which comprises administering to said mammal a therapeutically-effective amount of a compound of formula (II).

Other objects, features and advantages of the present invention will become apparent from the subsequent description and the appended claims.

Definitions

As used herein, the term, "$(C_1-C_8)$alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, isopentyl, neopentyl, heptyl, hexyl, octyl and the like. The term "$(C_1-C_8)$alkyl" encompasses "$(C_1-C_6)$alkyl".

The term "halo" means chloro, fluoro, bromo or iodo.

The term "$(C_1-C_6)$alkoxy" denotes a straight or branched alkyl chain having one to six carbon atoms attached to the remainder of the molecule by an oxygen atom. Typical $(C_1-C_6)$ alkoxy groups include methoxy, ethoxy, n-propoxy, isopropoxy, n-butoxy, t-butoxy, n-pentoxy, isopentoxy, neopentoxy and the like.

The term "$(C_3-C_8)$ cycloalkyl" referes to a hydrocarbon ring having the stated number of carbon atoms. Typical $(C_3-C_8)$ cycloalkyl groups include cyclopropyl, cyclobutyl, cyclopentyl, cyclohexyl, cycloheptyl, cyclooctyl.

The term, "$(C_2-C_8)$alkenyl," as used herein, means a straight chain or branched monovalent hydrocarbon group attached to the tetralin ring at any point on the chain, having the stated number range of carbon atoms and one double bond on the carbon attached to the tetralin ring. Typical groups include vinyl, prop-1-en-1-yl, isoprop-1-en-1-yl, n-but-2-en-2-yl, tertiary but-1-en-1-yl, isobut-1-en-1-yl, n-pent-1-en-1-yl, isopent-1-en-1-yl, pent-1-en-1-yl, hept-3-en-3-yl, hex-2-en-2-yl, oct-2-en-2-yl and the like.

The term, "$(C_1-C_8)$alkan-1-ol-1-yl" means a straight or branched chain monovalent hydrocarbon radical having the stated number of carbon atoms attached to the tetralin ring at the 1-position of the chain and, further, having an hydroxy group attached to the 1-position of the chain. Such groups include methan-1-ol-1-yl, ethan-1-ol-1-yl, n-propan-1-ol-1-yl, isopropan-ol-1-yl, n-butan-1-ol-1-yl, tertiary butan-1-ol-1-yl, isobutan-1-ol-1-yl, sec-butan-1-ol-1-yl, n-pentan-1-ol-1-yl, isopentan-1-ol-1-yl, neopentan-1-ol-1-yl, heptan-1-ol-1-yl, hexan-1-ol-1-yl, octan-1-ol-1-yl and the like.

Useful compounds for practicing the present invention includes pharmaceutically acceptable acid addition salts of the compounds defined by the above formulae I and II. Since the compounds of formula I are amines, they are basic in nature and accordingly react with any of a number of inorganic and organic acids to form pharmaceutically acceptable acid addition salts.

Acids commonly employed to form such salts are inorganic acids, such as hydrocholoric acid, hydrobomic acid, hydroiodic acid, sulfuric acid, phosphoric acid, and the like, and organic acids, such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts thus are the sulfate, pyrosolfate, bisulfate, sulfite, bisulfite, phosphate, monohydrogensphosphate, dihydrogenphosphate, metaphosphate, chloride, bromide, iodide, acetate, propionate, decanoate, caprylate, acrylate, formate, isobutyrate, caproate, heptanoate, propiolate, oxalate, malonate, succinate, suberate, sebacate, fumariate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, y-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid.

The compounds of the instant invention may have one stereocenter at the 2-position, and possibly more stereocenters, depending on the $R^3$ substituent at the 8-position, and may be isolated in optically active and racemic forms. The optically active isomers of the racemates of invention are also considered within the scope of Formulae I and II. Such optically active isomers may be prepared from their respective optically active precursors following the procedure described below, or by resolving the racemic mixtures. These resolutions can typically be carried out in the presence of a resolving agent, by chromatography or by repeated cyrstallization.

Procedures for separating racemates into their individual isomers can be found in references such as Jacques, et al., *Enantiomers, Racemates and Resolutions,* (John Wiley and Sons, New York 1981).

The term "amino-protecting group" is used herein as it is frequently used in synthetic organic chemistry, to refer to a group which will prevent an amino group from participating in a reaction carried out on some other functional group of the molecule, but which can be removed from the amine when it is desired to do so. In a similar fashion, the term "hydroxy protecting group" refers to a removable group which will prevent a hydroxy group from participating in a reaction performed on the molecule. Such groups are discussed by T. W. Greene in chapters 2 and 7 *of Protective Groups in Organic Synthesis,* John Wiley and Sons, New York, 1981, and by J. W. Barton in chapter 2 of *Protective Groups in Organic Chemistry,* J. F. W. McOmie, ed., Plenum Press, New York, 1973, which are incorporated herein by reference in their entirety. Examples of amino protecting groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. A preferred amino-blocking group is t-butoxycarbonyl.

Examples of hydroxy protecting groups include ether and substituted ether forming groups such as methyl, methoxymethyl, t-butoxymethyl, 1-ethoxyethyl and benzyl; silyl ether forming groups such as trimethylsilyl, triethylsilyl and methyl-diisopropylsilyl; ester forming groups such as formate, acetate and trichloroacetate and carbonate groups, such as methyl, 2,2,2-trichloroethylcarbonate and p-nitrophenyl carbonates.

The term "urinary incontinence" includes bacterial cystitis, interstitial cystitis, radiation/chemotherapy induced cystitis, outlet obstruction, neurogenic bladder, incontinence due to spinal cord injury and stroke, and nocturnal enurisis.

Preferred substituent groups of compounds of formulae I and II include the following:

(a) $R^1$ and $R^2$ are each independently hydrogen;
(b) $R^1$ and $R^2$ are each independently —$(C_1-C_6)$alkyl;
(c) $R^3$ is —$(C_1-C_8)$alkyl;
(d) $R^3$ is —$(CH_2)_nO(CH_2)_pR^5$;
(e) $R^3$ is —$(C_2-C_8)$alkenyl;

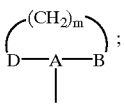

(f) $R^3$ is
(g) $R^3$ is

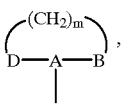

substituted with one substituent selected from the group consisting of —$(C_1-C_6)$alkyl or —$(C_3-C_8)$cycloalkyl;
(h) $R^5$ is —$(C_3-C_8)$cycloalkyl;
(i) $R^5$ is phenyl substituted with one substituent selected from the group consisting of —$(C_1-C_6)$alkyl or $(C_1-C_6)$alkoxy;
(j) $R^5$ is phenyl substituted with halo;
(k) A—B is >C=CH—;
(l) A—B is >CR$^4$CH$_2$—;
(m) D is CH$_2$;
(n) D is oxygen;
(o) m is 2–4;
(p) n is 1;
(q) p is 2; and
(r) q is 0 or 1.

A preferred genus of compounds include those compounds of formula I where:
$R^1$ and $R^2$ are each individually hydrogen or —$(C_1-C_6)$alkyl;
$R^3$ is

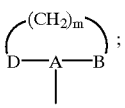

and
m is 2 or 3.

Of this preferred genus, compounds where A—B is >C=CH— are more preferred.

Still another preferred group of compounds include those where A—B is >CR$^4$CH$_2$— and D is —CH$_2$—.

The most preferred compound of the instant invention is 2-N,N-dimethylamino-8-(2-methylcyclopent-1-yl)tetralin hydrochloride.

Further typical examples of compounds of formula I which are useful in the present invention include:

2-N-methylamino-8-ethyltetralin;
2-N,N-dipropylamino-8-isopropyltetralin;
2-N-methyl-N-ethyl-8-pentyltetralin;
2-N,N-di-t-butylamino-8-isobutyltetralin;
2-N-ethyl-N-hexyl-8-octyltetralin;
2-N,N-dipropylamino-8-methyltetralin;
2-N-butylamino-8-eth-1-en-1-yltetralin;
2-N,N-dimethylamino-8-isoprop-1-en-1-yltetralin;

2-N-ethyl-N-methyl-8-but-1-en-1-yltetralin;
2-N,N-diethylamino-8-pent-1-en-1-yltetralin;
2-N-propylamino-8-hept-1-en-lyltetralin;
2-N-methyl-N-butyl-8-cyclopropylmethyloxymethyltetralin;
2-N,N-di-t-butyl-8-(2-cyclobutylethyl)oxymethyltetralin;
2-N-pentylamino-8-(2-(3-cyclopentylpropyl)oxy)ethyltetralin;
2-N-methyl-N-hexyl-8-(4-cyclohexylbutyl)oxytetralin;
2-N-methyltetralin-8-(4-(7-cyclooctylheptyl)oxy)butyltetralin;
2-N,N-dimethylamino-8-(3-(3-chlorophenyl)propyl)oxymethyltetralin;
2-N-ethyl-N-methylamino-8-(4-(4-methylphenyl)butyl)oxytetralin;
2-N-pentylamino-8-(3-(2-methoxyphenyl)methyloxy)propyltetralin;
2-N,N-diethylamino-8-(4-(3-(3-fluorophenyl)propyl)oxy)butyltetralin;
2-N-t-butyl-N-methylamino-8-(5-(4-ethylphenyl)pentyl)oxytetralin;
2-N-hexylamino-8-(5-(2-propoxyphenyl)heptyl)oxymethyltetralin;
2-N,N-dipropyl-8-(2-(6-(3-propylphenyl)hexyl)oxy) ethyltetralin;
2-N-methyl-N-butylamino-8-(4-(4-bromophenyl)butyl)oxymethyltetralin;
2-N-isopropylamino-8-(2-(2-hexylphenyl)ethyl)oxymethyltetralin;
2-N,N-diethyl-8-(3-(3-butoxyphenyl)) 2-N-ethyl-N-propylamino-8-cyclobutyltetralin;
2-N-t-butylamino-8-cyclopentyltetralin;
2-N,N-diethylamino-8-cycloheptyltetralin;
2-N-methyl-N-hexylamino-8-cyclooctyltetralin;
2-N-isopentylamino-8-cycloprop-1-en-1-yltetralin;
2,N,N-dibutylamino-8-cyclohex-1-en-1-yltetralin;
2-N-hexyl-N-ethylamino-8-cyclopent-1-en-1-yltetralin;
2-N-isobutylamino-8-(1'-hydroxy)cyclobutyltetralin;
2-N,N-dipentylamino-8(1'-hydroxy)cyclooctyltetralin; and
2-N-propyl-N-methylamino-8-(1'-hydroxy)cycloheptyltetralin.

Synthesis Methods

All of the reactions described in the following schemes are preferably conducted under an inert gas such as nitrogen.

The compounds of formula I where $R^3$ or $R^{3'}$ is —$(C_2$–$C_8)$ alkenyl,

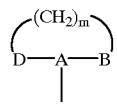

or

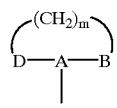

substituted with —$(C_1$–$C_6)$alkyl or —$(C_3$–$C_8)$cycloalkyl; where A—B is >C=CH— or >CR$^4$CH$_2$— and D is —CH$_2$— can be prepared according to the following reaction Scheme I.

Scheme I

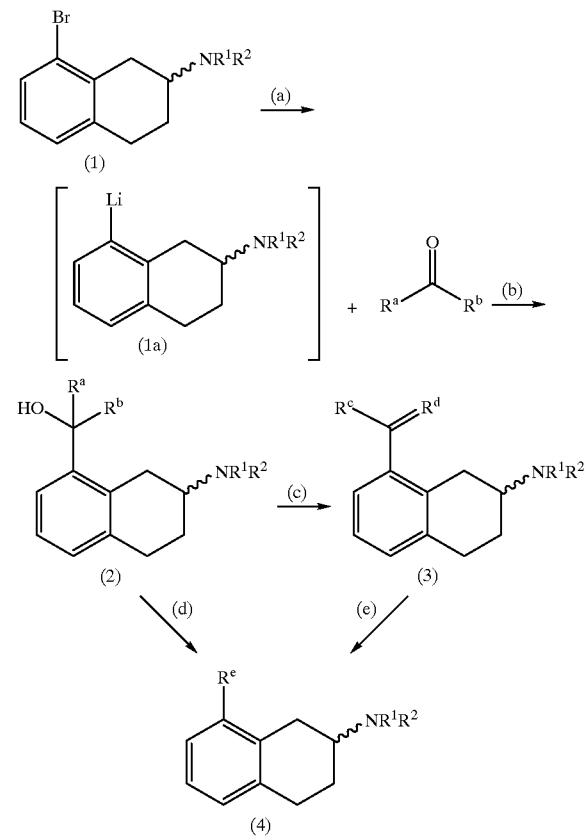

one of $R^a$ or $R^b$ is H and the other is —$(CH_2)_q(C_3$–$C_8)$ cycloalkyl, or $R^a$ and $R^b$ taken together are with the carbon to which they are attached are $(C_3$–$C_8)$alkyl or

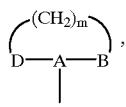

or substituted

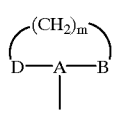

where A—B is >CR$^4$CH$_2$—, D is —CH$_2$— and R$^4$ is —OH;

$R^c$ and $R^d$ taken together with the carbon to which they are attached are $(C_2$–$C_8)$alkenyl or

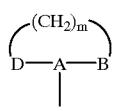

or substituted

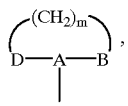, where A—B is >C=CH— and D is —CH$_2$—; R$_e$ is —(C$_1$-C$_8$)alkyl,

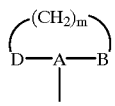

or substituted

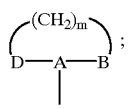;

where A—B is >CR$^4$CH$_2$—, D is —CH$_2$— and R$^4$ is hydrogen.

Compound (1), 8-bromo aminotetralin, is first treated with an organo-lithium reagent, preferably n-butyl lithium, to form the activated intermediate (1a). The reaction is carried out in a suitable solvent, preferably tetrahydrofuran or diethylether, at a temperature of about −78° C. and is substantially complete in 5 to 60 minutes.

In an aldol reaction, starting at a temperature of about −78° C., and gradually allowing to warm to a temperature of about 0° C., the lithiated intermediate (1a) is treated with an alkyl ketone or aldehyde or cyclic ketone of the formula R$^a$COR$^b$, where one of R$^a$ or R$^b$ is hydrogen and the other is —(CH$_2$)$_q$(C$_3$–C$_8$)cycloalkyl, or R$^a$ and R$^b$ taken together with the carbon to which they are attached form —(C$_1$–C$_8$)alkyl, or

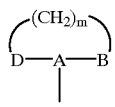

or substituted

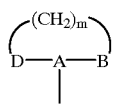

where A—B is >CR$^4$CH$_2$—, D is —CH$_2$— and R$^4$ is hydrogen, to form product (2), where R$^3$ is

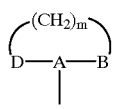

or substituted

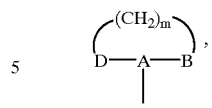,

A—B is >CR$^4$CH$_2$—, D is —CH$_2$— and R$^4$ is hydroxy. At temperatures of about 0° C., the reaction is substantially complete in about 10 minutes to an hour. Dehydration of (2) is achieved using trifluoroacetic acid to prepare product (3) where R$^3$ is —(C$_2$–C$_6$)alkenyl, —(CH$_2$)$_q$(C$_3$–C$_8$)cycloalkyl,

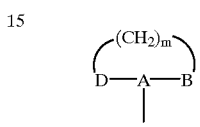

or substituted

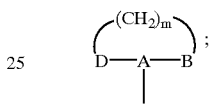;

where A—B is >C=CH— and D is —CH$_2$—.

Hydride reduction of (2), preferably using triethylsilane with trifluoroacetic acid or alternately, triethylsilane with a Lewis acid such as boron trifluoride etherate, can be employed to prepare (4), compounds of formula I where R$^3$ or R$^{3'}$ is

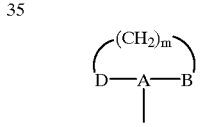

or substituted

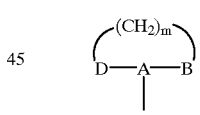

where A—B is >CR$_4$CH$_2$—, D is —CH$_2$—, and R$^4$ is hydrogen. Alternately, compound (3) can be hydrogenated by refluxing in an alcohol solvent with ammonium formate and palladium on carbon to prepare (4).

In step (b), for compounds where R$^3$ or R$^{3'}$ is methyl, the lithiated intermediate (1a) is treated with dimethylformamide instead a compound of formula R$^a$COR$^b$.

Compounds of formula I where R$^3$ or R$^{3'}$ is —(CH$_2$)$_n$O(CH$_2$)$_p$R$^5$, —(CH$_2$)$_n$O(CH$_2$)$_p$R$^{5'}$ or

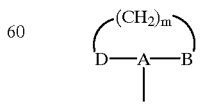

where A—B is >CR$^4$CH$_2$—, D is oxygen, R$^4$ is hydrogen and n is 1 to 4, both inclusive, can be prepared as follows in scheme II.

Scheme II

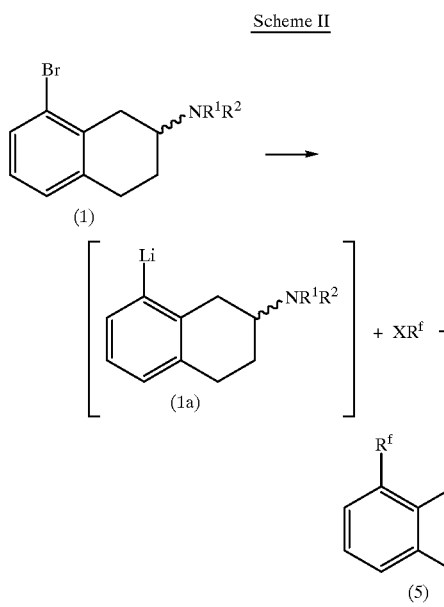

X is a halogen;

R$^f$ is —(CH$_2$)$_n$O(CH$_2$)$_p$R$^5$,

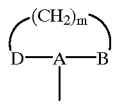

or substituted

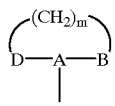

where A—B— is >CR$^4$CH$_2$—, D is oxygen and R$^4$ is hydrogen.

Following the procedure outlined in Scheme I, step (a) above, the brominated aminotetralin (1) is first activated by treatment with an organo-lithium reagent, such as n-butyl lithium to form (1a). The activated intermediate (1a) is then C-alkylated with an alkyl halide of the formula XR$^f$ where X is a halogen and R$^f$ is —(CH$_2$)$_n$O(CH$_2$)$_p$R$^5$, —(CH$_2$)$_n$O(CH$_2$)$_p$R$^{5'}$,

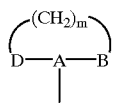

or substituted

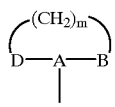

where A—B— is >CR$^4$CH$_2$—, D is oxygen and R$^4$ is hydrogen.

When R$^3$ is —(CH$_2$)$_n$O(CH$_2$)$_p$R$^5$ or —(CH$_2$)$_n$O(CH$_2$)$_p$R$^{5'}$ the halide starting material XR$^f$ may be prepared by reacting an appropriately substituted alcohol, HO(CH$_2$)$_n$O(CH$_2$)$_p$R$^5$ or HO(CH$_2$)$_n$O(CH$_2$)$_p$R$^{5'}$ with methoxymethyl chloride and a base, such as diisopropylethylamine or sodium or potassium carbonate in an organic solvent, such as methylene chloride or chloroform to form the methoxy intermediate. The methoxy group may then be replaced with an appropriate halogen, preferably chlorine, by reacting the intermediate with a halogenating agent such as boron trichloride.

For compounds where R$^3$ or R$^{3'}$ is

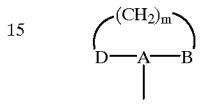

and D is oxygen, the alkyl halide starting material, XR$^f$, can be prepared by reacting a heterocyclic alkene,

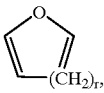

where r is an integer from 1 to 4 both inclusive, with a halogenating agent, such as hydrogen chloride gas to give

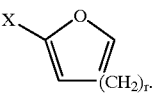

Compounds of formula I where R$^3$ or R$^{3'}$ is —(CH$_2$)$_n$O(CH$_2$)$_p$R$^5$ or —(CH$_2$)$_n$O(CH$_2$)$_p$R$^{5'}$ and n is zero, can be prepared as described in Scheme III as follows.

Scheme III

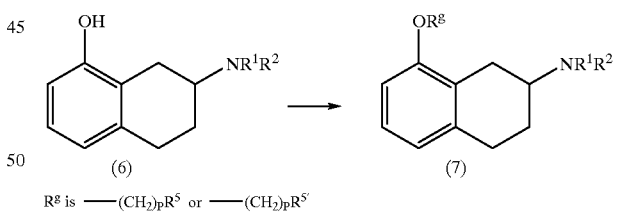

R$^g$ is ——(CH$_2$)$_p$R$^5$ or ——(CH$_2$)$_p$R$^{5'}$

An appropriately substituted phenol (6) is O-alkylated with an alkyl halide of the formula X(CH$_2$)$_p$R$^5$ or X(CH$_2$)$_p$R$^{5'}$ where X is preferably chlorine, in the presence of a base, such as potassium hydroxide or potassium carbonate and a catalyst such as potassium iodide, to form product (7). The reaction is preferably conducted in a solvent, such as ethanol, or solvent system, such as dimethoxyformamide/acetone.

Compounds of formula I may have one or two stereocenters; one at the 2-position of the tetralin ring and the other at the 8-position. Racemates of compounds of formula I, where R$^3$ or R$^{3'}$ is

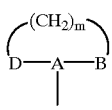

and D is oxygen, may be converted to their respective (R) and (S) enantiomers in a diastereoselective synthesis as described in Scheme IV below.

Scheme IV

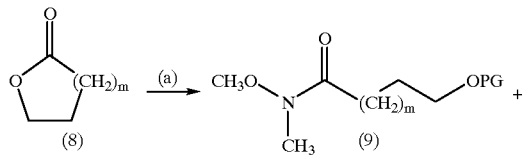

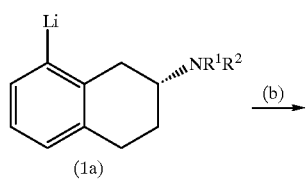

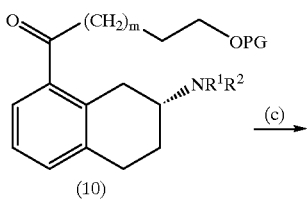

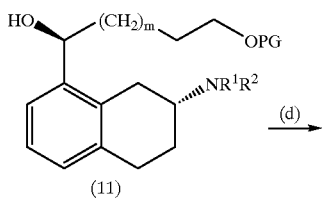

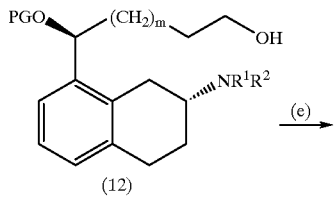

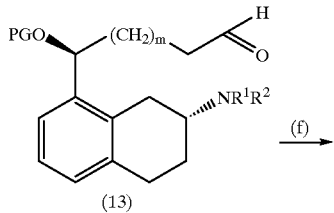

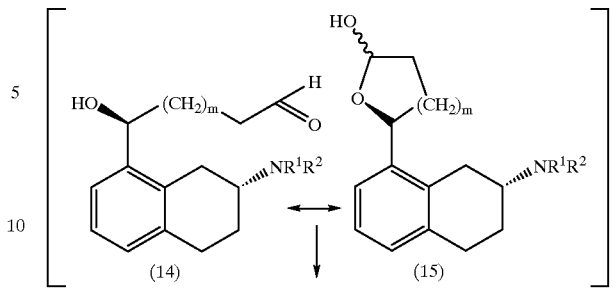

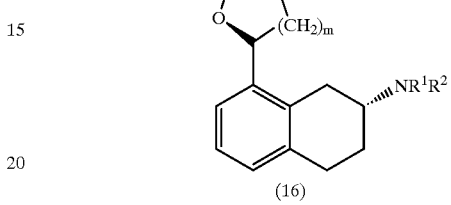

PG is an hydroxy protecting group

Starting material (8) is first treated with methoxymethyl amine and trimethyl aluminum, at temperatures of about −15° C. The terminal hydroxy is protected using, for example, butyldiphenylsilane to prepare intermediate (9). Intermediate (9) is then coupled with lithiated starting material (1a), preferably at temperatures of from about −78° C. to 0° C., in a solvent such as tetrahydrofuran, to prepare (10).

Stereospecific reduction of the carbonyl of (10) can be achieved by treatment with (−)DIP-Cl ((−) dimethylaminoisopropyl chloride) hydrochloride to produce the (R) enantiomer (11). The reaction is preferably conducted at temperatures of about −25° C. and is substantially complete in 1 to 3 days.

Protection of the alpha hydroxy can be accomplished by treating (11) with a selective hydroxy-protecting group, such as benzoylchloride, followed by removal of the silyl hydroxy-protecting group on the omega hydroxy, using, for example, tetrabutylammonium fluoride to prepare (12).

Oxidation of the omega hydroxy can then be readily accomplished using pyridinum chlorochromate to prepare (13). Removal of the alpha hydroxy protecting group and cyclization of (13) can then be accomplished by treatment with a strong base, such as sodium hydroxide.

Reduction of (15) is achieved using triethyl silane and trifluoroacetic acid to yield (16).

To achieve the (S) enantiomer, stereospecific reduction of the carbonyl of intermediate (11) can be accomplished using (S)-1,3,3-triphenyltetrahydro-1H,3H-pyrrolo[1,2-C][13,2] oxazaborole and boron trihydride in step (d) Scheme IV above instead of DIP-Cl.

The intermediates and final products may be isolated and purified by conventional techniques, for example by concentration of the solvents, followed by washing of the residue with water, then purification by conventional techniques such as chromatography or recrystallization.

It will be readily appreciated by the skilled artisan that the starting materials which are not described are either commercially available or can be readily prepared by known techniques from commercially available starting materials. All other reactants used to prepare the compounds in the instant invention are commercially available.

The pharmaceutically acceptable acid addition salts are typically formed by reacting an aminotetralin of formula I with an equimolar or excess amount of acid, preferably hydrochloric acid. The reactants are generally combined in a mutual solvent, such as diethyl ether or benzene, and the salt normally precipitates out of solution within about one hour to 10 days, and can be isolated by filtration.

The following examples further illustrate the preparation of the compounds of this invention. The examples are illustrative only and are not intended to limit the scope of the invention in any way.

The following abbreviations are used in the Examples below.

$NaHCO_3$ is sodium bicarbonate
$Na_2SO_4$ is sodium sulfate
$NH_4OH$ is ammonium hydroxide
HCl is hydrochloric acid
$MgSO_4$ is magnesium sulfate
$CH_2Cl_2$ is methylene chloride
MeOH is methanol
NaOH is sodium hydroxide
DMAP dimethylaminopyridine
THF is tetrahydrofuran
N-BuLi is n-butyllithium
$Et_3SiH$ is triethylsilane
$BF_3$ is borom trifluoride
$CF_3COOH$ trifluoroacetic acid
EtOH is ethanol
Pd/C is palladium on carbon
$NH_4OH$ is ammonium hydroxide
$NH_4CO_2H$ is ammonium formate
$AlMe_3$ is trimethyl aluminum
$Na_2CO_3$ is sodium carbonate
$BH_3$ is borane
Et2O is diethylether

EXAMPLE 1

(R)-2-N,N-dimethylamino-8-methyltetralin hydrochloride

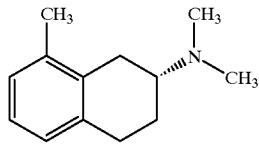

A. Preparation of (R)-2-N,N-dimethylamino-8-formyltetralin

[Reaction under nitrogen atmosphere, using flame dried glassware]

To 1.004 g of (+)-(R)-2-N,N-dimethylamino-8-bromotetralin, dissolved in 15 mL of dry THF and chilled to −78° C. in a dry ice/acetone bath, was added 3.45 mL (1.6 M) of n-BuLi, and the mixture was allowed to stir for one hour. Anhydrous dimethylformamide (0.46 mL) was then added via syringe. The reaction was allowed to slowly return to room temperature. Water was added and the mixture was extracted with ethyl acetate. The organic layers were dried over $MgSO_4$ and concentrated to leave a yellow oil that was purified by silica gel flash column chromatography using a solvent mixture (10% MeOH, 0.5% $NH_4OH$ in $CH_2Cl_2$) to give 683 mg of (R)-2-N,N-dimethylamino-8-formyltetralin (85%), which was used for next step without further characterization.

B. Preparation of (R)-2-N,N-dimethylamino-8-methyltetralin hydrochloride

The compound of part A, above (660 mg) was dissolved in 8 mL of dry $CH_2Cl_2$ and 9.3 mL of $Et_3SiH$ was added. To this vigorously stirring solution was bubbled $BF_3$ gas via syringe. The resulting solution oiled out to a yellow sludge and the solution cleared from yellow to a clear liquid. The reaction was allowed to stir overnight. After quenching with 20 mL of saturated $NaHCO_3$ and diluting with 50 mL of $CH_2Cl_2$, the layers were separated and the organic layer was washed with brine. The organics were then dried over $MgSO_4$, filtered, and evaporated to recover an oily yellow solid. The crude product was purified by silica gel flash column chromatography using a solvent mixture (6.5% MeOH, 0.5% $NH_4OH$ in $CH_2Cl_2$). The HCl salt was made from this oily residue and recrystallized from hot EtOH and $Et_2O$.

M.P.: 180–181° C. dec
HRMS Calculated: 190.1596
Found: 190.157

EXAMPLE 2

(R)-2-N,N-dimethylamino-8-(cyclobut-1-en-1-yl) tetralin

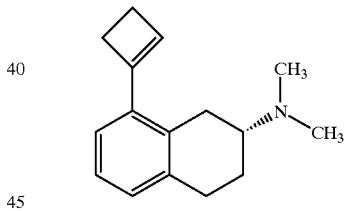

A. Preparation of (R)-2-N,N-dimethylamino-8-(1'-hydroxy)cyclobutyltetralin hydrochloride

[Reaction under nitrogen atmosphere, using flame dried glassware]

By substantially following the procedure in Example 1, part A, using 1.50 g of (+)-(R)-2-N,N-dimethylamino-8-bromotetralin, 5.2 ml of n-BuLi (1.6M, 1.4 eq) and 0.75 mL of cyclobutanone (1.7 eq.), subtitled compound was prepared, 1.09 g (75%).

B. Preparation of (R)-2-N,N-dimethylamino-8-(cyclobut-1-en-1-yl)tetralin hydrochloride Compound of part A above (1.09 g) was dissolved in 20 mL of dry $CH_2Cl_2$ and chilled to 0° C. $CF_3COOH$, 2.2 mL, was then added dropwise. The reaction stirred for 15 minutes at 0° C. before it was allowed to warm to room temperature over 2.3 hours. The reaction was quenched with 20 mL of NaOH (2N) and 80 mL of $CH_2Cl_2$. The organic phase was washed with water, dried over $MgSO_4$, filtered, and evaporated to give 1.07 g of as a crude oil. Flash column purification over silica gel using a solvent mixture (6.5% MeOH, 0.5% NH$_4$OH in CH$_2$Cl$_2$) afforded 827 mg of (R)-2-N,N-dimethylamino-8-(cyclobut-1-enyl)tetralin. The HCl salt was made with 205 mg of the material. The salt was recrystallized from hot EtOH and (ether/hexane) to recover 159 mg of (R)-2-N,N-dimethylamino-8-(cyclobut-1-en-1-yl)tetralin hydrochloride.

M.P.: 196–197° C. dec

Elemental Analysis:

Calculated: C, 72.85; H, 8.41; N, 5.31

Found C, 72.59; H, 8.37; N, 5.43

EXAMPLE 3

(R)-2-N,N-dimethylamino-8-(prop-1-en-2-yl tetralin) hydrochloride

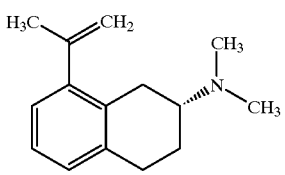

Title compound was prepared substantially according to the procedure of Example 2 using 1.50 g (5.9 mmol) of (+)-(R)-2-N,N-dimethylamino-8-bromotetralin and 0.74 mL of acetone to give 682 mg of (R)-2-N,N-dimethylamino-8-(prop-1-en-2-yl-tetralin) as a free base which was converted to the HCl salt.

M.P.: 168–170° C.

Elemental Analysis:

Calculated: C, 71.55; H, 8.81; N, 5.56

Found: C, 71.66; H, 8.95; N, 5.57

EXAMPLE 4

(R)-2-N,N-dimethylamino-8-(cyclooct-1-en-1-yl) tetralin hydrochloride

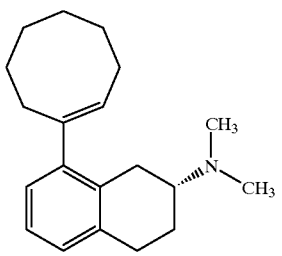

Title compound was prepared substantially according to the procedure of Example 2 using 1.70 g (6.71 mmol) of (+)-(R)-2-N,N-dimethylamino-8-bromotetralin and 1.5 mL of cyclooctanone to give 444 mg of (R)-2-N,N-dimethylamino-8-(cyclooct-1-en-1-yl)tetralin, and was recovered as the HCl salt.

M.P.: 174–176° C.

Elemental Analysis

Calculated: C, 75.09; H, 9.45; N, 4.38

Found: C, 75.06; H, 9.21; N, 4.48

EXAMPLE 5

(R)-2-N,N-dimethylamino-8-(pent-2-en-3-yl)tetralin hydrochloride

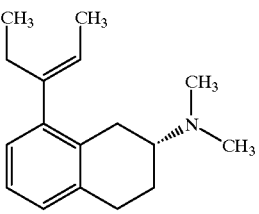

Title compound was prepared substantially according to the procedure of Example 2 using 953 mg (3.75 mmol) of (+)-(R)-2-N,N-dimethylamino-8-bromotetralin and 0.68 mL of diethyl ketone to give 373 mg of (R)-2-N,N-dimethylamino-8-(pent-2-en-3-yl)tetralin hydrochloride.

M.P.: 158–160° C.

Elemental Analysis:

Calculated: C, 72.96; H, 9.37; N, 5.01

Found: C, 72.74; H, 9.22; N, 5.07

EXAMPLE 6

(R,S), (R,R)-2-N,N-dimethylamino-8-(3-methylcyclopent-1-en-1-yl)tetralin hydrochloride

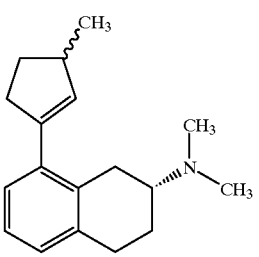

Title compounds were prepared substantially according to the procedure of Example 2 using 602 mg (2.37 mmol) of (+)-(R)-2-N,N-dimethylamino-8-bromotetralin and 4.03 mL of 3-methylcyclopentanone to give 229 mg of a mixture of two diasteromers of (R,S),(R,R)-2-N,N-dimethylamino-8-(3-methylcylopent-1-en-1-yl)tetralin hydrochloride which was isolated as the HCl salt.

M.P.: 160–162° C.

Elemental Analysis:

Calculated: C, 73.82; H, 9.13; N, 5.01

Found: C, 74.08; H, 8.98; N, 4.80

EXAMPLE 7

(R)-2-N,N-dimethylamino-8-cyclobutyltetralin hydrochloride

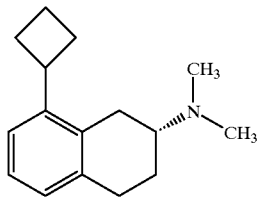

The compound of Example 2, 621 mg, was dissolved in 30 mL of MeOH along with 200 mg of Pd/C (5%) and 10 equivalents of ammonium formate. The mixture was stirred at reflux for 5 hours before allowing it to cool to room temperature. The resulting mixture was filtered over diatomaceous earth and the filter cake was rinsed with warm methanol. The filtrate was concentrated and redissolved in methylene chloride. The organic layer was washed with water (pH ~11) and brine, and then dried over magnesium sulfate, filtered, and evaporated. The crude oil was made into its corresponding HCl salt and recrystallized from hot EtOH and (ether/hexanes) to recover 150 mg (R)-2-N,N-dimethylamino-8-cyclobutyltetralin hydrochloride.

M.P.: 155–156° C.

Elemental Analysis

Calculated: C, 72.29; H, 9.10; N, 5.27

Found: C, 72.50; H, 9.15; N, 5.57

EXAMPLE 8

(R,S),(R,R)-2-N,N-dimethylamino-8-(2-cyclopentylcyclopent-1-yl)tetralin hydrochloride

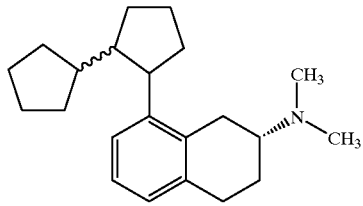

Title compound was prepared substantially according to the procedure of Examples 2 and 7 using 466 mg of (+)-(R)-2-N,N-dimethylamino-8-bromotetralin and 0.616 mL of (R,S)-2-cyclopentyl cyclopeatanine. A mixture of two diastereomers (R,S),(R,R)-2-N,N-dimethylamino-8-(2-cyclopentylcyclopent-1-yl)tetralin, 108 mg, was isolated as the HCl salt.

M.P.: 172–174° C.

Elemental Analysis

Calculated: C, 76.38; H, 9.32; N, 4.05

Found: C, 76.13; H, 9.59; N, 3.97

EXAMPLE 9

(R,S),(R,R)-2-N,N-dimethylamino-8-(2-methylcyclopent-1-yl)tetralin hydrochloride

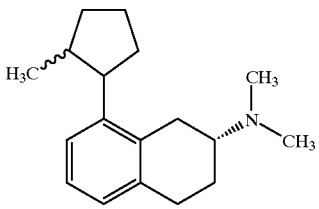

Title compound was prepared substantially according to the procedure of Examples 2 and 7 using 400 mg (1.57 mmol) of (+)-(R)-2-N,N-dimethylamino-8-bromotetralin and 0.202 mL of 2-methylcyclopentanone to give 39 mg of a mixture of two diastereomers (R,S),(R,R)-2-N,N-dimethylamino-8-(2-methylcyclopent-1-yl)tetralin which was isolated as the HCl salt.

M.P.: 181–183° C.

Elemental Analysis

Calculated: C, 73.57; H, 9.60; N, 4.77

Found: C, 73.29; H, 9.64; N, 4.69

EXAMPLE 10

(R)-2-N,N-dimethylamino-8-cyclohexylmethyl tetralin hydrochloride

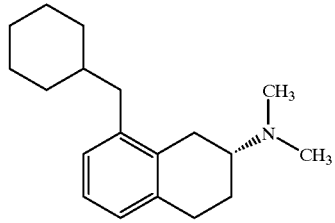

Title compound was prepared substantially according to the procedure of Examples 2 and 7 using 627 mg (2.47 mmol) of (+)-(R)-2-N,N-dimethylamino-8-bromotetralin and 0.509 mL cyclohexanecarboxaldehyde to give (R)-2-N,N-dimethylamino-8-cyclohexylmethyltetralin, 356 mg of which was isolated as the HCl salt.

M.P.: 234–235° C.

Elemental Analysis

Calculated: C, 74.12; H, 9.82; N, 4.55

Found: C, 73.89; H, 9.68; N, 4.40

EXAMPLE 11

(R)-2-N,N-dimethylamino-8-cyclooctyltetralin hydrochloride

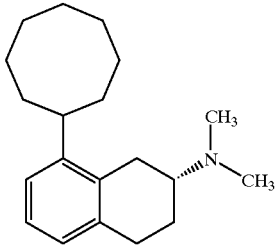

Title compound was prepared substantially according to the procedure of Example 7 using 303 mg (1.07 mmol) of (R)-2-N,N-dimethylamino-8-cyclooct-1-en-1-yl-tetralin hydrochloride. Title compound, 210 mg, was recovered as the HCl salt.

M.P.: 171–173° C.

Elemental Analysis:

Calculated: C, 74.02; H, 10.02; N, 4.35

Found: C, 74.40; H, 9.97; N, 4.55

EXAMPLE 12

(R)-2-N,N-dimethylamino-8-methoxyethoxymethyl tetralin hydrochloride

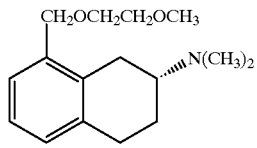

To a stirred solution of (+)-(R)-2-N,N-dimethylamino-8-bromotetralin (1.67 mmol) in 9 mL of THF was added n-butyllithium (1.76 mmol) at −78° C. under nitrogen. After stirring for 45 minutes, methoxyethoxymethyl chloride (1.75 mmol) was added. The resulting mixture was stirred at −78° C. for 15 minutes and then gradually warmed to room temperature over a period of 1 hour. Ten ml of 5% NaHCO$_3$ solution was added. The mixture was extracted with CH$_2$Cl$_2$ (15 mL×3). The combined organic layer was dried (Na$_2$SO$_4$), filtered, and then concentrated. The crude residue was purified by flash chromatogrphy using a mixture of solvents (NH$_4$OH, 0.5%; MeOH, 7%; in CH$_2$Cl$_2$) to give 382.7 mg (87%) of title compound.

MS (m/e): 263 (M$^+$).

HCl salt of the product has melting point, of 147–148° C.

EXAMPLE 13

(R,S),(R,R)-2-N,N-dimethylamino-8-(tetrahydropyran-2-yl)tetralin hydrochloride

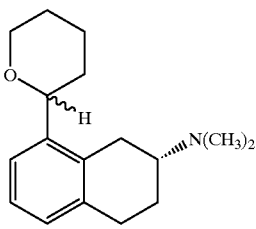

A. Preparation of 2-chlorotetrahydropyran

The starting material of 2-chlorotetrahydropyran was synthesized by reported procedures (R. A. Earl, L. B. Townsend; *Synthesis*, 1972, 1140). Dihydropyran (300 mmol) and CH$_2$Cl$_2$ (25 mL) were placed in a flask. HCl gas was bubbled through the precooled mixture (−78° C.) for 30 minutes. The mixture was then slowly warmed to room temperature. Distillation of the crude product (44° C./water aspirator) gave 20.4 g (56% purity) of 2-chlorotetrahydropyran.

B. Preparation of (R,S)(R,R)-2-N,N-dimethylamino-8-(tetrahydropyran-2-yl)tetralin hydrochloride To a stirred solution of (+)-(R)-2-N,N-dimethylamino-8-bromotetralin (1.10 mmol) in 5 mL of THF was added n-butyllithium (1.32 mmol) at −78° C. under nitrogen. After stirring for 45 minutes, 2-chlorotetrahydropyran (1.20 mmol) was added. The resulting mixture was stirred at −78° C. for 15 minutes and then gradually warmed to room temperature over a period of 1 hour. Ten mL of 5% NaHCO$_3$ solution was added. The mixture was extracted with CH$_2$Cl$_2$ (15 mL×3). The combined organic layer was dried (Na$_2$SO$_4$), filtered, and then concentrated. The crude residue was purified by flash chromatography using a mixture of solvent (NH$_4$OH, 0.5%; MeOH, 7%; in CH$_2$Cl$_2$) to give 116.4 mg (45%) of title compound a mixture of two diastereoisomers. HCl salts of the products were prepared.

Ms (m/e): 296 (M$^+$).

Elemental Analysis:

Calculated: C, 69.02; H, 8.86; N, 4.73

Found: C, 69.21; H, 9.10; N, 4.67

EXAMPLE 14

(R)-2-N,N-dimethylamino-8-(tetrahydrofuran-2-yl)tetralin hydrochloride

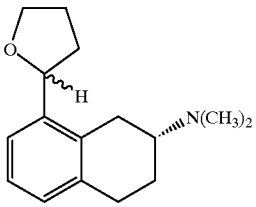

A. Preparation of 2-chlorotetrahydrofuran

Subtitled product was prepared substantially according to the procedures reported in part A of Example 16. Thus, the reaction of dihydrofuran (400 mmol) and HCl gas in CH$_2$Cl$_2$ gave 28.2 g (66%) of 2-chlorotetrahydrofuran.

B. Preparation of (R)-2-N,N-dimethylamino-8-(tetrahydrofuran-2-yl)tetralin hydrochloride Using substantially the same procedure as in Example 13, part B, the reaction of (+)-(R)-2-N,N-dimethylamino-8-bromotetralin (1.28 mmol) with n-butyllithium (1.54 mmol) and 2-chlorotetrahydrofuran (1.53 mmol) in 5 mL of THF gave 175.1 mg (56%) of title compound as a mixture of the two diastereoisomers. HCl salts of the products were prepared.

MS (m/e): 246° (M$^+$).

Elemental Analysis:

Calculated: C, 68.19; H, 8.58; N, 4.97

Found: C, 68.38; H, 8.68; N, 4.85

EXAMPLE 15

(R)-2-N,N-dimethylamino-8-(1'-hydroxycyclohexyl) tetralin hydrobromide

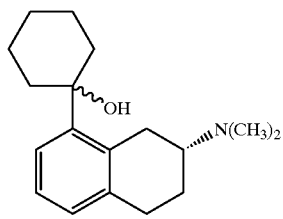

To a stirred solution of (+)-(R)-2-N,N-dimethylamino-8-bromotetralin (4.17 mmol) in 15 mL of THF, was added n-butyllithium (1.6 M in hexanes, 5.76 mmol) at −78° C. under nitrogen. After stirring for 45 minutes, cyclohexanone (6.37 mmol) was added. The resulting mixture was stirred at −78° C. for 30 minutes and then gradually warmed to room temperature over a period of 30 minutes. The reaction mixture was quenched with 5% NaHCO$_3$ solution (25 mL), then extracted with CH$_2$Cl$_2$ (20 mL×3). The combined organic layer was dried (Na$_2$SO$_4$), filtered, and then concentrated. The crude residue was purified by flash chromatography using a mixture of NH$_4$OH, MeOH, CH$_2$Cl$_2$ (0.5%: 9%: 90.5%) to give 751.6 mg (66%) of title compound as an oil.

MS (m/e): 256° (M$^+$−H$_2$O)

HBr salt of the product has melting point of 210–211° C.

EXAMPLE 16

(R)-2-N,N-dimethylamino-8-(1'-hydroxy cycloheptyl)tetralin hydrobromide

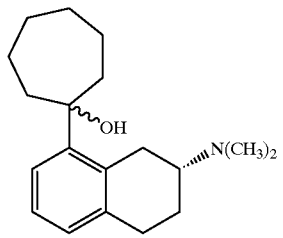

Following substantially the same procedure as described in Example 15, the reaction of (+)-(R)-2-N,N-dimethylamino-8-bromotetralin (4.06 mmol) with n-butyllithium (5.66 mmol) and cycloheptanone (6.10 mmol) in 15 mL of THF gave 696.8 mg (60%) of title compound.

MS (m/e) 270° (M$^+$−H$_2$O)

HBr salt of the products has melting point of 186–187° C.

EXAMPLE 17

(R)-2-N,N-dimethylamino-8-(cyclohex-1-en-1-yl) tetralin hydrochloride

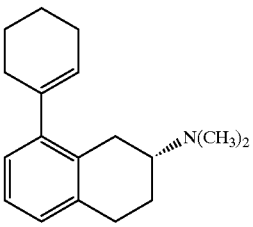

A mixture of the compound of Example 15 (1.29 mmol) and trifluoroborane etherate (1.38 mmol) in 10 mL of CH$_2$Cl$_2$ was stirred at room temperature for 5 minutes. NaOH solution (1N, 10 mL) was added. The product was extracted with CH$_2$Cl$_2$. The extract was dried, filtered, and concentrated. The crude residue was purified by flash chromatography using a mixture of NH$_4$OH, MeOH, and CH$_2$Cl$_2$ (0.5: 10: 120) to give 56% yield of title compound.

The HCl salt of the product has melting point of 190–191° C.

Elemental Analysis:

Calculated: C, 74.08; H, 8.98; N, 4.80

Found: C, 74.29; H, 8.89; N, 5.01

EXAMPLE 18

(R)-2-N,N-dimethylamino-8-(cyclohept-1-en-1-yl) tetralin hydrochloride

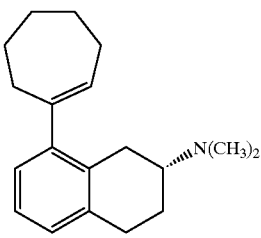

Using a substantially same procedure as described in Example 17, using (1.67 mmol) of the compound of Example 16, and trifluoroacetic acid (0.3 ML) in 8 mL of CH$_2$Cl$_2$ gave 80% yield of title compound.

HCl salt of the product has melting point of 160–161° C.

Elemental Analysis:

Calculated: C, 74.61; H, 9.23; N, 4.58

Found: C, 74.85; H, 9.25; N, 4.78

EXAMPLE 19

(R)-2-N,N-dimethylamino-8-(cyclopent-1-en-1-yl)tetralin hydrochloride

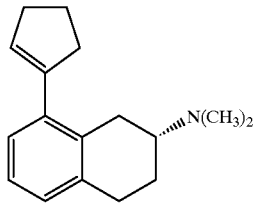

A. Preparation of (R)-8-(1'-hydroxy)cyclopentyl-2-N,N-dimethylaminotetralin (R)-8-(1'-hydroxy)cyclopentyl-2-N,N-dimethylaminotetralin was prepared substantially according to the procedures described in Example 15 using (+)-(R)-2-N,N-dimethyamino-8-bromotetralin (5.99 mmol) with n-butyllithium (8.32 mmol) and cyclopentanone (10.17 mmol) in 17 mL of THF to give 815.6 mg (53%) of sub-titled product.

B. Preparation of (R)-2-N,N-dimethylamino-8-(cyclopentyl-1-en-1-yl)tetralin hydrochloride Using a substantially same procedure as described in Example 17, (3.07 mmol) of the compound of part A, above, and trifluoroacetic acid (1.5 mL) in 20 mL of $CH_2Cl_2$ gave 659.2 mg (80%) of title compound.

HCL salt of the product has melting point of 184–185° C.

Elemental Analysis:

Calculated: C, 73.49; H, 8.71; N, 5.04

Found: C, 73.27; H, 8.51; N, 5.27

EXAMPLE 20

(R)-2-N,N-dimethylamino-8-cyclopentyltetralin hydrochloride

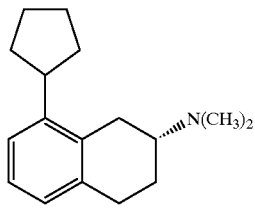

To a stirred solution of the compound of Example 20 (0.41 mmol) and EtSiH (0.63 mmol) in 11 mL of $CH_2Cl_2$, was added trifluoroborane etherate (0.81 mmol) at room temperature. The resulting mixture was stirred at room temperature for 2 hours. Saturated $Na_2CO_3$ (15 mL) was added. The product was extracted with $CH_2Cl_2$. The extract was dried, filtered, and concentrated. The crude residue was purified by flash chromatography using a mixture of NH4OH, MeOH, $CH_2Cl_2$ (0.5: 5: 95) to give 73.0 mg (73%) of title compound.

HCl salt of the product has melting point of 158–159° C.

MS (m/e): 244° (M+H).

EXAMPLE 21

(R)-2-N,N-dimethylamino-8-cyclohexyltetralin hydrochloride

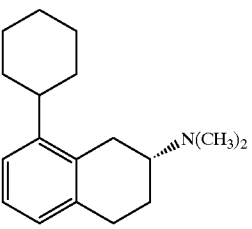

The compound of Example 17 (1.29 mmol) was hydrogenated (60 PSI $H_2$) in ethanol (25 mL) in the presence of catalyst Pd/C (5%, 80 mg) for 12 hours. The crude mixture was filtered and then evaporated. The residue was purified by flash chromatography using a mixture of $NH_4OH$, methanol, and $CH_2Cl_2$ (0.5: 6: 94) to give 243.2 mg (73%) of title product.

HCl salt of the product has melting point of 213–214° C.

Elemental Analysis:

Calculated: C, 73.57; H, 9.60; N, 4.78

Found: C, 73.49; H, 9.57; N, 4.96

EXAMPLE 22

(R)-2-N,N-dimethylamino-8-cycloheptyltetralin hydrochloride

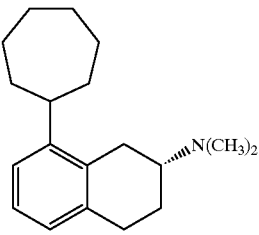

The compound of Example 18 (1.08 mmol) was hydrogenated (60 PSI $H_2$) in ethanol (25 mL) in the presence of catalyst Pd/C (5%, 75 mg) for 12 hours. The crude mixture was filtered and then evaporated. The residue was purified by flash chromatography using a mixture of $NH_4OH$, methanol, and $CH_2Cl_2$ (0.5: 6: 94) to give 211.7 mg (73%) of title product.

HCl salt of the product has melting point of 192–193° C.

Elemental Analysis:

Calculated: C, 74.12; H, 9.82; N, 4.55

Found: C, 73.93; H, 9.76; N, 4.78

EXAMPLE 23

2-(R)-2'-(S)-N,N-dimethylamino-8-(tetrahydrofuran-2-yl)tetralin hydrochloride

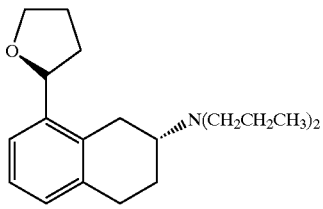

A. Preparation of N-methyl-N-methoxy-4-t-butyldiphenylsilyloxybutylamide

To a stirred solution of n-methyl-N-methoxyamine hydrochloride (107.12 mmol) in 100 mL of $CH_2Cl_2$, was added 2.0 M solution of $AlMe_3$ (62.5 mmol) at −15° C. under nitrogen. After the mixture was stirred for 40 minutes, γ-butyrolactone (31.25 mmol) was added at −15° C. The resulting mixture was stirred at room temperature for 2.5 hours. HCl solution (1 N) was added dropwise until all the precipitate was dissolved. The mixture was extracted with $CH_2Cl_2$/MeOH (9:1; 50 mL×8). The combined organic layer was dried, filtered, and concentrated. Without further purification, the crude residue containing N-methyl-N-methoxy-4-hydroxybutylamide was treated with chloro-t-butyldiphenylsilane (34.6 mmol) and imidazole (38.19 mmol) in the presence of DMAP (1.23 mmol) and DMF (50 mL) at room temperature under nitrogen for 13 hours. Upon aqueous workup, the crude residue was purified by flash chromatography using a mixture of hexanes and ethyl acetate (4:1) to give subtitled product (7.98 g) in 66% overall yield.

B. Preparation of (+)-(R)-2-N,N-dimethylaminotetralin-8-yl-(3'-t-butyldiphenylsilyloxy)propylketone To a stirred solution of (+)-(R)-2-N,N-dimethylamino-8-bromotetralin (1.36 mmol) in 6 mL of THF was added n-butyllithium (1.6 M in hexanes, 1.6 mmol) at −78° C. under nitrogen. After stirred for 30 minutes, the compound of part A (1.43 mmol) in 4 mL of THF was added. The resulting mixture was stirred at −78° C. for 20 minutes and then at room temperature for 2 hours. After aqueous workup, the crude residue was purified by flash chromatography using a mixture of $NH_4OH$, $CH_2Cl_2$ and MeOH (0.5: 6: 94) to give subtitled product (170 mg) in 25% yield.

C. Preparation of 2-(R)-1'-(S)-2-N,N-dimethylamino-8-(1'-hydroxy-3'-t-butyldiphenylsilyloxy)propyltetralin To a stirred solution of the compound of part B, above, (0.67 mmol) in 1.5 mL of THF was added (−)-DIP-Cl(0.81 mmol) at 25° C. After the mixture was stirred for 3 days, the solvent was removed by evaporation. The residue was purified by flash chromatography using a mixture of $NH_4OH$, MeOH, and $CH_2Cl_2$ (0.5: 8: 92) to give 107.6 mg (32%) of subtitled product.

D. Preparation of 2-(R)-1'-(S)-2-N,N-dimethylamino-8-(1'-benzoyloxy-3'-t-butyldiphenylsilyloxy)propyltetralin To a stirred solution of the compound of part C (0.64 mmol) in 6 mL of $CH_2Cl_2$ were added 0.2 mL of pyridine and 0.1 mL of benzoyl chloride (0.86 mmol). The mixture was stirred at room temperature for 3 hours. Saturated $Na_2CO_3$ (10 mL) was added. The product was extracted with $CH_2Cl_2$. The extract was dried, filtered, and concentrated. The residue was purified by flash chromatography using a mixture of $NH_4OH$, MeOH, and $CH_2Cl_2$ (0.5:8:92) to give subtitled product (0.64 mmol) (363.9 mg) in 94% yield.

E. Preparation of 2-(R)-1'-(S)-2-N,N-dimethylamino-8-(1'-benzoyloxy-3'-hydroxy)propyltetralin To a stirred solution of the compound of part D (0.60 mmol) in 6 mL of THF was added tetrabutylammonium fluoride (1.20 mmol). The mixture was stirred at room temperature for 5 hours. After aqueous workup, the crude residue was purified by flash chromatography using a mixture of $NH_4OH$, MeOH, and $CH_2Cl_2$ (0.5:10:90) to give subtitled product (0.54 mmol) in 91% yield.

F. Preparation of 2'-(R)-4-(S)-4-[2'-N,N-dimethylaminotetralin]-8'-yl-4-benzoyloxybutyraldehyde To a stirred solution of the compound of part E (0.207 mmol) in $CH_2Cl_2$ (2 mL) was added pyridinium chlorochromate (0.414 mmol) at room temperature. The mixture was stirred for 45 minutes. NaOH solution (2N) was added to basify the mixture (pH=12). The product was extracted with $CH_2Cl_2$. The extract was dried, filtered, and concentrated. Purification of the residue by flash chromatography using a mixture of $NH_4OH$, MeOH, and $CH_2Cl_2$ (0.5:8:92) gave subtitled product (21.8 mg) in 29% yield.

G. Preparation of 2-(R)-2'-(S)-2-N,N-dimethylamino-8-(5'-hydroxytetrahydrofuran-2'-yl)tetralin To a stirred solution of the compound of part F (21.8 mg) in MeOH (3 mL) was added NaOH (1N, 3 mL). The mixture was stirred at room temperature for 50 minutes. The product was extracted with $CH_2Cl_2$ (10 mL×3). The extract was dried, filtered, and concentrated to give 15.5 mg of subtitled product as a crude product.

H. Preparation of 2-(R)-2'-(S)-N,N-dimethylamino-8-(tetrahydrofuran-2-yl)tetralin hydrochloride To a stirred solution of the compound of part G, above, (15.5 mg, 0.06 mmol) in 3 mL of $CH_2Cl_2$ were added $Et_3SiH$ (0.2 mL) and trifluoroacetic acid (0.2 mL). The mixture was stirred at room temperature for 10 minutes. NaOH solution was added until the pH equaled 12–14. The product was extracted with $CH_2Cl_2$ (10 mL×3). The combined organic layer was dried, filtered, and concentrated. The residue was purified by flash chromatography using a mixture of $NH_4OH$, MeOH, and $CH_2Cl_2$ (0.5:8:92) to give title product (8.2 mg) in 57% yield.

MS (m/e): 246 (M+H).

HCl salt of the product has melting point of 186–188° C.

EXAMPLE 24

2-(R)-2'(R)-N,N-dimethylamino-8-(tetrahydrofuran-2-yl)tetralin hydrochloride

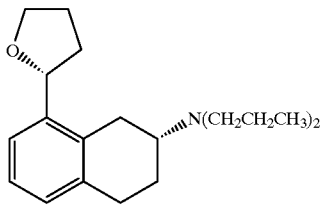

A. Preparation of 2-(R)-1'-(R)-2-N,N-dimethylamino-8-(1'-hydroxy-3'-t-butyldiphenylsilyloxy)propyltetralin To a stirred solution of (+)-(R)-2-N,N-dimethylaminotetralin-8-yl-(3'-t-butyldiphenylsilyloxy)propylketone (0.47 mmol) (Example 30, Part B) and (S)-1,3,3-triphenyltetrahydro-1H, 3H-pyrrolo[1,2-C][1,3,2] oxazaborole (0.09 mmol) in 6 mL of THF was added $BH_3$ solution in THF (0.50 mmol) at 0° C. under nitrogen. The mixture was stirred for 30 minutes. The solvent was evaporated and the residue was dissolved in ether (10 mL) and methanol (10 mL). Diethanolamine (2 mL) was added. The mixture was heated to reflux for 14 hours. $NH_4OH$ solution was added to basify the mixture. The product was extracted with $CH_2Cl_2$. The extract was dried, filtered, and concentrated. The residue was purified by flash chromatography using a mixture of $NH_4OH$, MeOH, and $CH_2Cl_2$ (0.5:6:94) to give 88.5 mg of subtitled product.

B. Preparation of 2-(R)-1'-(R)-2-N,N-dimethylamino-8-(1'-benzoyloxy-3'-t-butyldiphenylsilyloxy)propyltetralin To a stirred solution of the compound of part A (0.568 mmol) in 8 mL of $CH_2Cl_2$ were added 0.3 mL of pyridine and 0.1 mL of benzoyl chloride (0.86 mmol). The mixture was stirred at room temperature for 3 hours. Saturated $Na_2CO_3$ (10 mL) was added. The product was extracted with $Ch_2Cl_2$. The extract was dried, filtered, and concentrated. The residue was purified by flash chromatography using a mixture of $NH_4OH$, MeOH, and $CH_2Cl_2$ (0.5:8:92) to give subtitled product (0.64 mmol) (308.0 mg) in 90% yield.

C. Preparation of 2-(R)-1'-(R)-2-N,N-dimethylamino-8-(1'-benzoyloxy-3'-hydroxy)propyltetralin To a stirred solution of the compound of part B, above, (0.51 mmol) in 6 mL of THF was added tetrabutylammonium fluoride (1.02 mmol). The mixture was stirred at room temperature for 5 hours. After aqueous workup, the crude residue was purified by flash chromatography using a mixture of $NH_4OH$, MeOH, and $CH_2Cl_2$ (0.5:10:90) to give subtitled product (0.47 mmol) in 92% yield.

D. Preparation of 2'-(R)-4-(R)-4-[2'-N,N-dimethylaminotetralin]-8'-yl-4-benzoyloxybutyraldehyde To a stirred solution of the compound of part C (0.466 mmol) in $CH_2Cl_2$ (5 mL) was added pyridinium chlorochromate (0.932 mmol) at room temperature. The mixture was stirred for 45 minutes. NaOH solution (2N) was added to basify the mixture (pH=12). The product was extracted with $Ch_2Cl_2$. The extract was dried, filtered, and concentrated. Purification of the residue by flash chromatography using a mixture of $NH_4OH$, MeOH, and $CH_2Cl_2$ (0.5:8:92) gave subtitled product (61 mg).

E. Preparation of 2-(R)-2'-(R)-2-N,N-dimethylamino-8-(5'-hydroxytetrahydrofuran-2'-yl) tetralin To a stirred solution of the compound of part D (61 mg) in MeOH (10 mL) was added NaOH (1N, 6 mL). The mixture was stirred at room temperature for 50 minutes. The product was extracted with $CH_2Cl_2$ (15 mL×3). The extract was dried, filtered, and concentrated to give 35 mg of subtitled compound as a crude product.

F. Preparation of 2-(R)-2'-(R)-N,N-dimethylamino-8-(tetrahydrofuran-2-yl)tetralin hydrochloride To a stirred solution of the compound of part E (35 mg) in 5 mL of $CH_2Cl_2$ were added $Et_3SiH$ (0.3 mL) and trifluoroacetic acid (0.3 mL). The mixture was stirred at room temperature for 10 minutes. NaOH solution was added until pH=12–14. The product was extracted with $CH_2Cl_2$ (10 mL×3). The combined organic layer was dried, filtered, and concentrated. The residue was purified by flash chromatography using a mixture of $NH_4OH$, MeOH, and $CH_2Cl_2$ (0.5:8:92) to give title product (21.0 mg).

MS (m/e): 245 ($M^+$).

HCl salt of the product has melting point of 195–197° C.

EXAMPLE 25

(R)-2-N,N-dimethylamino-8-(4-fluorophenyl) ethyloxymethyltetralin hydrochloride

Following substantially the same procedure as described in Example 15, the reaction of (+)-(R)-2-N,N-dimethylamino-8-bromotetralin (475 mg, 1.87 mm) with n-butyllithium (2.24 mmol) and 4-fluorophenethyl chloromethyl ether (389 mg, 2.06 mm) in 1 mL of THF gave 88.4 mg of the desired product.

HCl salt of the product has melting point of 109–111° C.

Elemental Analysis: Calculated: C, 69.31; H, 7.48; N, 3.85; Found: C, 69.56; H, 7.46; N, 4.04.

EXAMPLE 26

(R)-2-N,N-dimethylamino-8-(4-bromophenyl) ethyloxymethyltetralin hydrochloride

Following substantially similar procedure as described in Example 15, the reaction of (+)-(R)-2-N,N-dimethylamino-8-bromotetralin (435 mg, 1.71 mmol) with n-butyllithium (2.05 mmol) and 4-bromophenethyl chloromethyl ether (512 mg, 1.88 mmol) in 12 mL of THF gave 201 mg of the desired product.

HCl salt of the product has melting point of 114–115° C.

Elemental Analysis: Calculated: C, 59.38; H, 6.41; N, 3.30; Found: C, 59.12; H, 6.21; N, 3.28.

EXAMPLE 27

(R)-2-N,N-dimethylamino-8-(4-methoxyphenyl) ethyloxymethyltetralin hydrochloride Following substantially the same procedure as described in Example 15, the reaction of (+)-(R)-2-N,N- dimethylamino-8-bromotetralin (395.7 mg, 1.557 mm) with n-butyllithium (1.07 ml) and 4-methoxyphenethyl chloromethyl ether (351 mg, 1.635 mm) in 1 mL of THF gave 117 mg of the desired product.

HCl salt of the product has melting point of 131–132° C.

Elemental Analysis: Calculated: C, 70.84; H, 8.27; N, 3.59; Found: C, 70.81; H, 8.37; N, 3.59.

The method of this invention is practiced by administering to a mammal a direct acting 5-$HT_{1D\alpha}$ agonist or a pharmaceutically acceptable salt thereof. The phrase "direct acting 5$TH_{1D\alpha}$ agonist" as used in this specification and these claims means a non-endogenous chemical compound and includes: (1) synthetic chemical compounds (ligands) that mimic the action of serotonin on 5-$HT_{1D\alpha}$ receptors by directly activating these receptors; and (2) partial agonists, which are synthetic chemical compounds (ligands) that mimic the action of serotonin on 5-$HT_{1D\alpha}$ receptors by directly activating these receptors but produce a smaller maximal effect than do other ligands that act on the same receptor. These compounds may have activity at other receptors but must have some component of 5-$HT_{1D\alpha}$ agonist activity.

Assay Experiments

The ability of the compounds of this invention to bind to the 5-$HT_{1D\alpha}$ receptor subtype was measured essentially as described in N. Adham, et al., *Proceedings of the National Academy of Sciences (USA)*, 90, 408–412 (1993).

Membrane Preparation: Membranes were prepared from transfected Ltk-cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-$HT_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 mL of buffer (50 mM Tris, 10 mM $MgCl_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. Representative compounds of the invention exhibited an Ki at the 5-$HT_{1D\alpha}$ receptor of at least 100 μmol.

As was reported by R. L. Weinshank, et al., WO093/14201, the 5-$HT_{1D}$ receptor is functionally coupled to a G-protein as measured by the ability of serotonin and serotonergic drugs to inhibit forskolin stimulated cAMP production in NIH3T3 cells transfected with the 5-$HT_{1D}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.

Measurement of cAMP Formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% $CO_2$. Drug dose-effect curves were then conducted by adding 6 different final concentrations of drug, followed immediately by the addition of forskolin (10 mM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds were tested and found to be agonists at the 5-$HT_{1D\alpha}$ receptor in the cAMP assay.

Pharmaceutical Formulations of the Invention

The therapeutic and prophylactic treatments provided by this invention are practiced by administering to a mammal in need thereof a dose of a compound of formula I or II, or a pharmaceutically acceptable salt thereof, that is effective in activating the 5-$HT_{1D\alpha}$ receptor.

While it is possible to administer a compound employed in the methods of this invention directly without any formulation, the compounds are usually administered in the form of pharmaceutical formulation comprising a pharmaceutically acceptable excipient and at least one compound of the present invention. The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See, e.g., Remington's Pharmaceutical Sciences, (16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets and injectable solutions. Especially preferred are capsules and tablets.

The therapeutic and prophylactic treatments provided by this invention are practiced by administering to a mammal in need thereof a dose of a compound of formula I or a pharmaceutically acceptable salt or solvate thereof that is effective to alleviate the pathological effects of $5-HT_{1D\alpha}$ receptor-activated diseases.

Advantageously for this purpose, formulations may be provided in unit dosage form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The following formulation examples may employ as active compounds any of the compounds of this invention. The examples are illustrative only and are not intended to limit the scope of the invention in any way.

Formulation 1

Hard gelatin capsules are prepared using the following ingredients:

|  | Quantity (mg/capsule) |
|---|---|
| (R)-2-N-methyl-N-hexylamino-8-cyclooctyltetralin | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| (R)-2-N-isopentylamino-8-(1-oxacyclopropyl)tetralin | 250 |
| Cellulose, microcrystalline | 400 |

|  | Quantity (mg/tablet) |
|---|---|
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| (R)-2-N,N-di-t-butylamino-8-isobutyltetralin | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| (R)-2-N-propylamino-8-hept-1-en-lyltetralin | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| (R)-2-N-methyl-N-propylamino-8-(4-bromophenyl)butyloxymethyl tetralin | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| (R)-2-N,N-dimethylamino-8-(3-chlorophenyl)propyloxymethyltetralin | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| (R)-2-N-ethyl-N-methylamino-8-(4-methylphenyl)butyloxytetralin | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| (R)-2-N,N-dipropyl-8-(3-propylphenyl)hexyloxyethyltetralin hydrochloride | 100 mg |
|---|---|
| Isotonic saline | 1,000 ml |

The solution of the above ingredients generally is administered intravenously to a subject at a rate of 1 ml per minute.

We claim:
1. A compound of the formula (I)

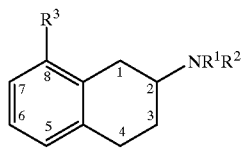

(I)

wherein:
R$^1$ and R$^2$ are each individually hydrogen or —(C$_1$–C$_6$) alkyl;
R$^3$ is —(C$_2$–C$_8$)alkenyl, —(CH$_2$)$_q$(C$_3$–C$_8$)cycloalkyl, —(CH$_2$)$_n$O(CH$_2$)$_p$R$^5$,

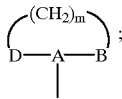

or

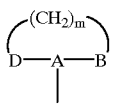

substituted with one substituent selected from the group consisting of —(C$_1$–C$_6$)alkyl and —(C$_3$–C$_8$) cycloalkyl;
where
A—B is >C=CH— or >CR$^4$CH$_2$—;
D is —CH$_2$— or oxygen;
R$^4$ is hydrogen or —OH;
R5 is —(C$_3$–C$_8$)cycloalkyl, or phenyl substituted with one substituent selected from the group consisting of halo, —(C$_1$–C$_6$)alkyl and (C$_1$–C$_6$)alkoxy;
m is an integer from 1 to 5 both inclusive;
n is an integer from 0 to 4 both inclusive;
p is an integer from 1 to 7 both inclusive; and
q is an integer from 0 to 4 both inclusive;
or a pharmaceutically acceptable salt or optical isomer thereof;
provided that when D is oxygen, >A—B is not >C=CH—; and when R$^4$ is —OH, D is not oxygen.

2. A compound of formula I as claimed in claim 1 wherein R$^1$ and R$^2$ are each individually hydrogen or —(C$_1$–C$_6$) alkyl;
R$^3$ is

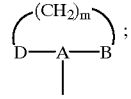

and
m is 2 or 3.

3. A compound of formula I as claimed in claim 2 wherein A—B— are >C=CH— or >CR$^4$CH$_2$—.

4. A compound of formula I as claimed in claim 3 wherein A—B— is >CR$^4$CH$_2$— and D is —CH$_2$—.

5. A compound of claim 4 which is (R)-2-N,N-dimethylamino-8-(2-methylcyclopent-1-yl)tetralin hydrochloride.

6. A pharmaceutical formulation comprising a compound of formula I as claimed in claim 1 together with a pharmaceutically acceptable carrier or diluent therefor.

7. A method of alleviating the pathological effects of 5-HT$_{1D\alpha}$ receptor activated diseases in a mammal selected from dementia, Parkinson's Disease, appetite modulation, anxiety, migraine, sexual dysfunction, irritative bladder symptoms of benign prostatic hyperplasia, urge incontinence and excessive bladder activity, caused by bacterial cystitis, interstitial cystitis, radiation/chemotherapy-induced cystitis, outlet obstruction, neurogenic bladder, spinal cord injury, stroke, and nocturnal enurisis in a mammal which comprises administering to the mammal a therapeutically effective amount of a compound as claimed in claim 1.

* * * * *